United States Patent [19]

Lue et al.

[11] Patent Number: 4,739,764
[45] Date of Patent: Apr. 26, 1988

[54] METHOD FOR STIMULATING PELVIC FLOOR MUSCLES FOR REGULATING PELVIC VISCERA

[75] Inventors: Tom Lue, Millbrae; Emil A. Tanagho, San Rafael; Richard Schmidt, San Francisco; Curtis A. Gleason, Palo Alto, all of Calif.

[73] Assignee: The Regents of the University of California, Berkeley, Calif.

[21] Appl. No.: 855,085

[22] Filed: Apr. 22, 1986

Related U.S. Application Data

[63] Continuation-in-part of Ser. No. 611,836, May 18, 1984, Pat. No. 4,607,639.

[51] Int. Cl.⁴ .............................................. A61N 1/36
[52] U.S. Cl. ............................ 128/419 R; 128/419 E; 128/784
[58] Field of Search ........... 128/419 E, 419 R, 423 R, 128/783, 788, 794, 799

[56] References Cited

U.S. PATENT DOCUMENTS

| | | | |
|---|---|---|---|
| 3,650,276 | 3/1972 | Burghele et al. | 128/419 E |
| 3,667,477 | 6/1972 | Susset et al. | 128/419 E |
| 4,569,351 | 2/1986 | Tang | 128/419 E |

OTHER PUBLICATIONS

Ingersoll et al., "American Journal of Physiology", vol. 189, 1957, pp. 167-172, 128/419E
Bors, "Journal of Urology," vol. 67, Jun. 1952, pp. 925-935, 128/419E.

Primary Examiner—William E. Kamm
Attorney, Agent, or Firm—Phillips, Moore, Lempio & Finley

[57] ABSTRACT

Applicant's U.S. patent application Ser. No. 611,836, now U.S. Pat. No. 4,607,639, describes a method for controlling the function of a bladder, including identification of selected nerve bundles controlling the separate functions of the bladder and its external sphincter and the application of pulse trains to one or more electrodes positioned on the nerve bundles to control the functions of the bladder and external sphincter. The methods taught herein utilize similar method steps for modulating symptoms resulting from a loss of coordination between the normally synchronized functions of a bladder and bowel and their associated sphincters. The methods are also used for treating incontinence by increasing sphincter tonus. The use of similar method steps for controlling evacuation of the bowel is also disclosed.

35 Claims, 15 Drawing Sheets

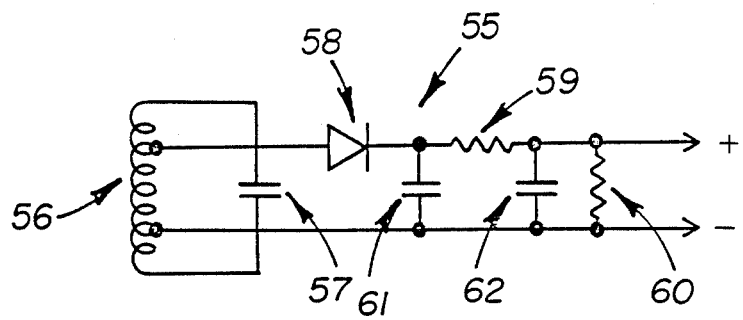
FIGURE 13
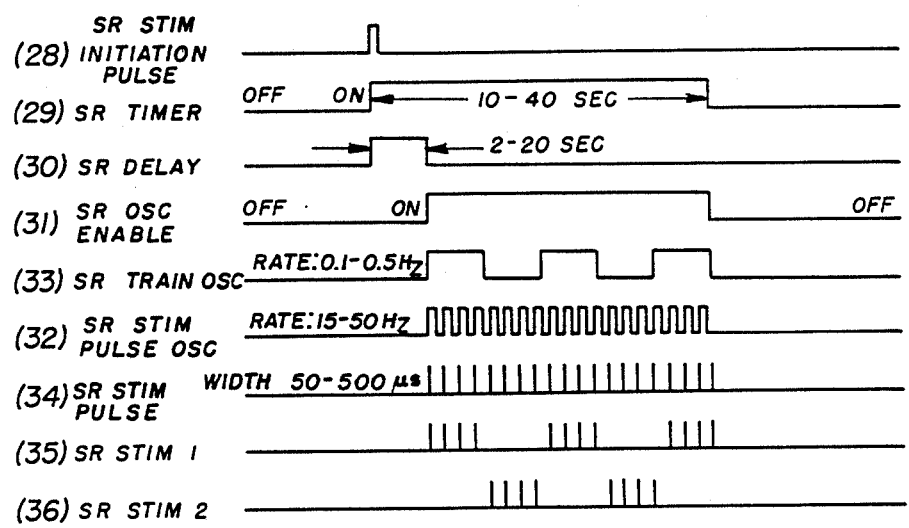
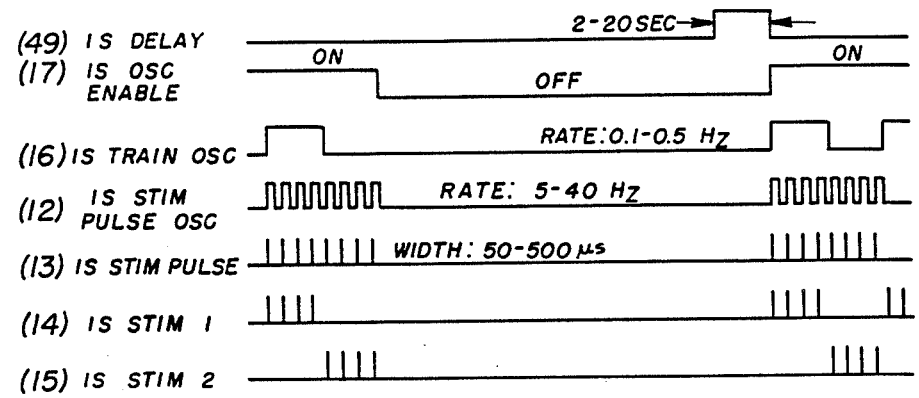
SR = SACRAL ROOT
IS = INFERIOR SOMATIC
OSC = OSCILLATOR
FIGURE 14

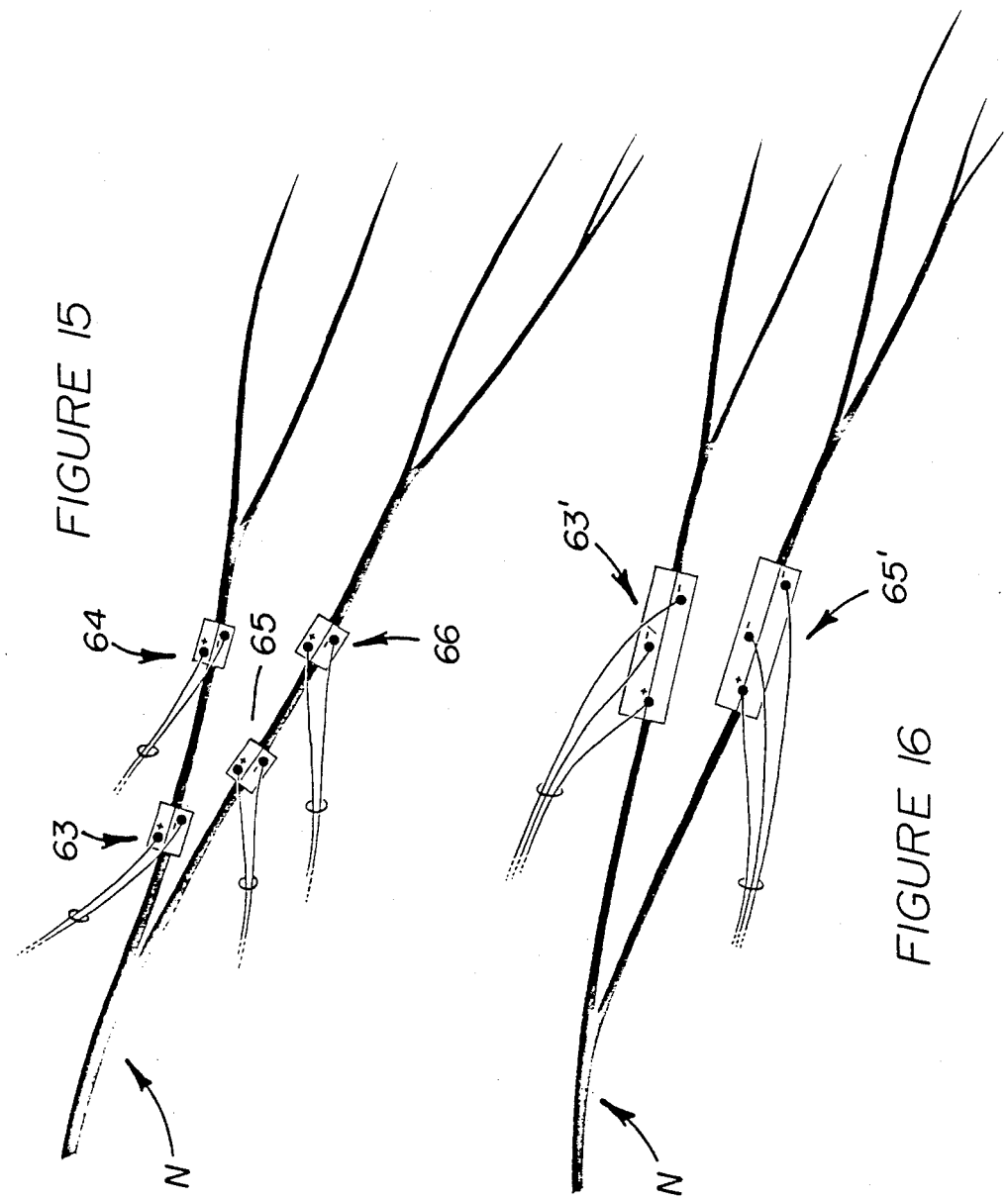

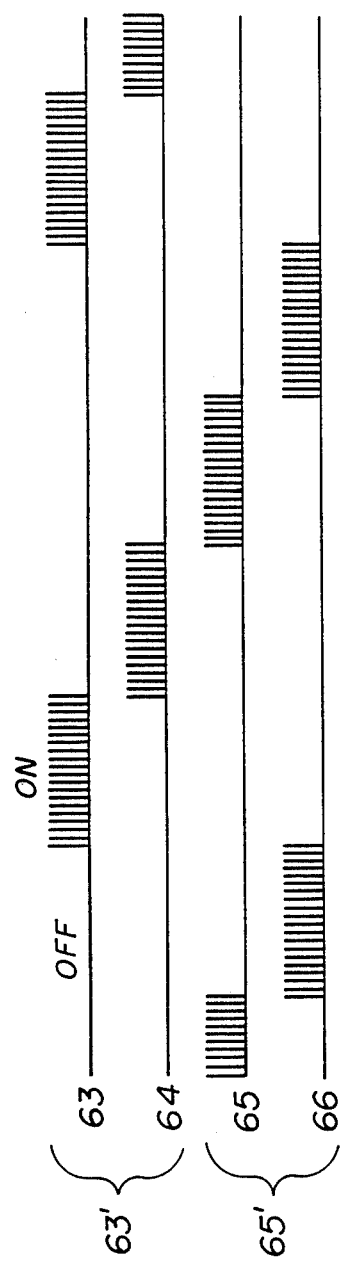

METHOD FOR STIMULATING PELVIC FLOOR MUSCLES FOR REGULATING PELVIC VISCERA

ACKNOWLEDGEMENT

This invention was made with government support under Grant Nos. NS 2307 and R01 18029-04 awarded by the Department of Health and Human Services. The Government has certain rights in this invention.

CROSS-REFERENCE TO RELATED APPLICATION

This application is a continuation in part of U.S. patent application Ser. No. 611,836, filed on May 18, 1984 for "Method and System for Controlling Bladder Evacuation," now U.S. Pat. No. 4,607,639.

TECHNICAL FIELD

This invention relates generally to a method for regulating and treating bodily functions and, more particularly, to the utilization of one or more electrodes on selected nerve bundles and the application of pulse trains to the electrode(s) to regulate or treat such functions.

BACKGROUND ART

Various medical patients exhibit involuntary control over their bladder and/or bowel. Although vesicostomy or an artificial sphincter implanted around the urethra are commonly used to provide partial control over the evacuation function of the bladder and to control continence, these solutions have drawbacks well known to those skilled in the medical profession and related arts. Other patients who achieve a modicum of control over their bladder functions are equally in need of a system to rehabilitate their nerve and muscle dysfunctions. Similar problems arise in respect to involuntary bowel control.

The physiology of the bladder and bowel is closely linked to the urethral muscle physiology of the pelvic floor (levator ani muscle) and its related urethral and anal sphincters. For the bladder to store urine and for the bowel to serve as a reservoir for feces, two opposite, but complementary, behaviors are found. In particular, the bladder and rectum must relax and the urethral and anal sphincters must remain contracted. The reverse is true during evacuation of either urine or feces, i.e., the urethral or anal sphincter will relax, along with the pelvic floor, and subsequently the bladder and rectum will contract.

The sequence will reverse once voiding and defecation is completed, i.e., the sphincters and pelvic floor muscles will revert to their tonic closure states and the bladder and rectum will revert to their storage states. This behavior has been demonstrated by simultaneous manometric (or EMG/pressure) recordings of this bladder/rectum, urethral/anal behavior during filling and emptying of the bladder. This sequence of events is well-established and is accepted universally.

DISCLOSURE OF INVENTION

Applicants U.S. patent application Ser. No. 611,836, now U.S. Pat. No. 4,607,639, describes methods for controlling the function of the bladder, with such methods also being adapted to "effect control of other organs, such as the bowel, colon and associated sphincters, (e.g., anus) and cuffs." In reference to FIG. 4, such application also states that the described procedure "will normally provide means for selectively eliminating or supressing spasting detrusor activity, spastic urethal and pelvic floor activity and spastic anal sphincter." This application describes specific methods for stimulating pelvic floor muscles to modulate symptoms resulting from a loss of coordination between the normally synchronized functions of the bladder and bowel and for treating incontinence by increasing sphincter tonus. Also, a method for controlling bowel evacuation is disclosed.

This invention extends the teachings of parent U.S. patent application Ser. No. 611,836 now U.S. Pat. No. 4,607,639 by disclosing twenty-one specific methods for modulating the symptoms resulting from a loss of coordination between normally synchronized functions of visceral organs and seven methods for treating incontinence by increasing sphincter tonus. The term "controlling" as used herein not only includes the selective control of the bladder's and/or bowel's evacuation and related sphincter functions on a continuous basis, but further includes isolated or periodic control of such functions for diagnostic or rehabilitation purposes, e.g., neuromodulation of muscular behavior to rehabilitate muscular dysfunction in the pelvic floor without stimulating the pelvic nerve controlling the bladder's detrusor muscle. The term "organn" as used herein broadly means an independent part of the human body that performs a special function or functions, including visceral organs such as the bladder, bowel and colon and associated sphincters and cuffs.

In one aspect, the method of this invention comprises the identification of the anatomical location and functional characteristics of selected nerve bundles controlling the separate function of at least one organ, including a person's bladder, rectum and/or associated sphincters. Electrode means is then positioned on such nerve bundles for electrically stimulating the nerve bundles while simultaneously isolating adjacent nerve bundles therefrom. Pulse trains are sequentially applied to the electrode means to separately control the function of the one organ or a number of organs simultaneously. In the preferred embodiments of this invention, the positioning step comprises attaching two or more electrodes in twenty-one different combinations on selected nerve bundles for modulation purposes and in seven locations on selected nerve bundles for increasing sphincter tonus. Each method disclosed can be carried forth either bilaterally or unilaterally, depending on a particular patient's needs.

In another aspect of this invention, the method taught in applicant's parent U.S. patent application Ser. No. 611,836 now U.S. Pat. No. 4,607,639 is utilized to control the coordinated and synchronized function of a bowel and associated sphincter.

BRIEF DESCRIPTION OF THE DRAWINGS

Other advantages and objects of this invention will become apparent from the following description and accompanying drawings wherein:

FIG. 13 schematically illustrates a typical electronic circuit for use in an implantable receiver of the FIG. 12 micturition control system;

FIG. 14 diagramatically illustrates electronic signals and their time relationship for the FIG. 12 micturition control system;

FIG. 15 illustrates an electrode arrangement including pairs of electrodes attached to separate nerve fibers and adapted for use with the FIG. 12 control system;

FIG. 16 is a view similar to FIG. 15, but illustrates a multiplicity of active electrode contacts on single electrodes;

FIG. 17 diagramatically illustrates electrical impulses in their timed relationship for the electrode arrangements illustrated in FIGS. 15 and 16.

GENERAL DESCRIPTION AND COMMON SUBJECT MATTER

Figures 1, 2:
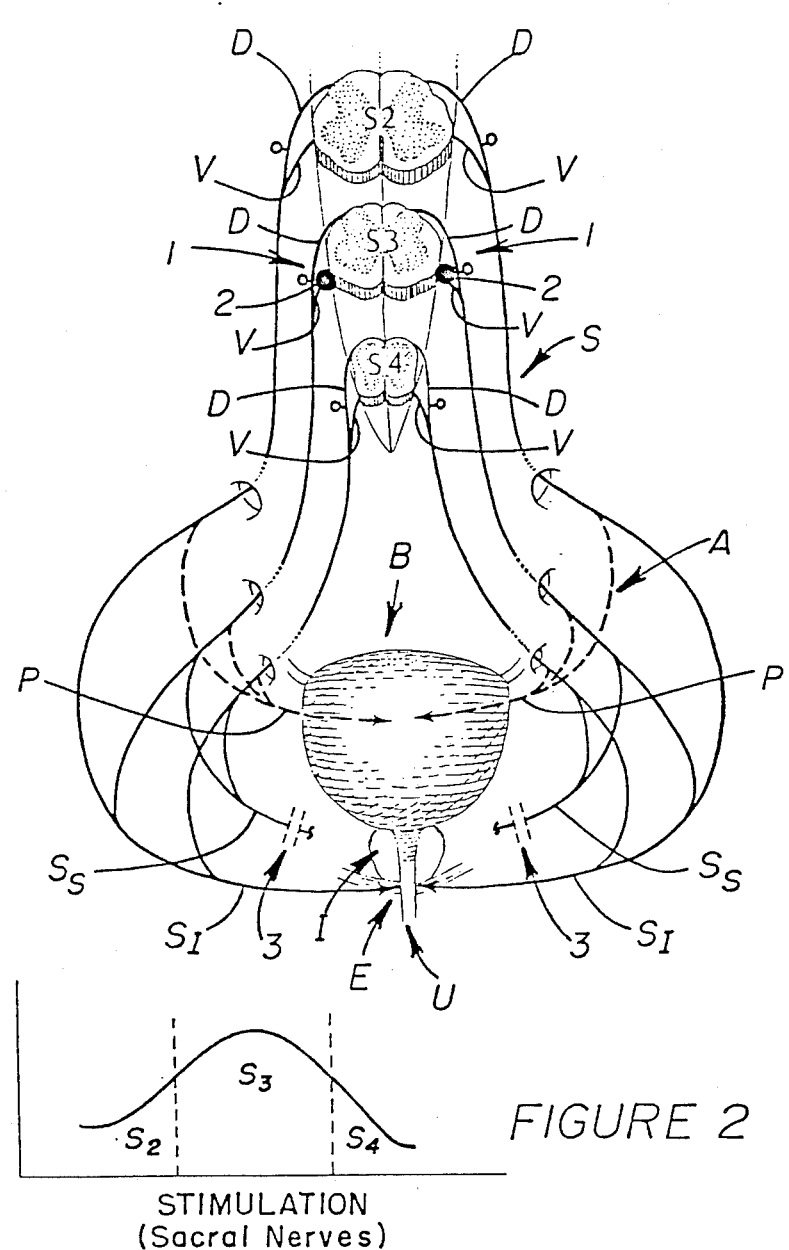
FIG. 1 schematically illustrates the pelvic plexus region in a human, including the nervous system for controlling bladder evacuation and related functions, and further illustrates a first operative procedure for controlling such functions.
FIG. 2 schematically illustrates a stimulation-response curve of bladder contraction in response to stimulation of the S2, S3 and S4 sacral nerves.
Figure 3:
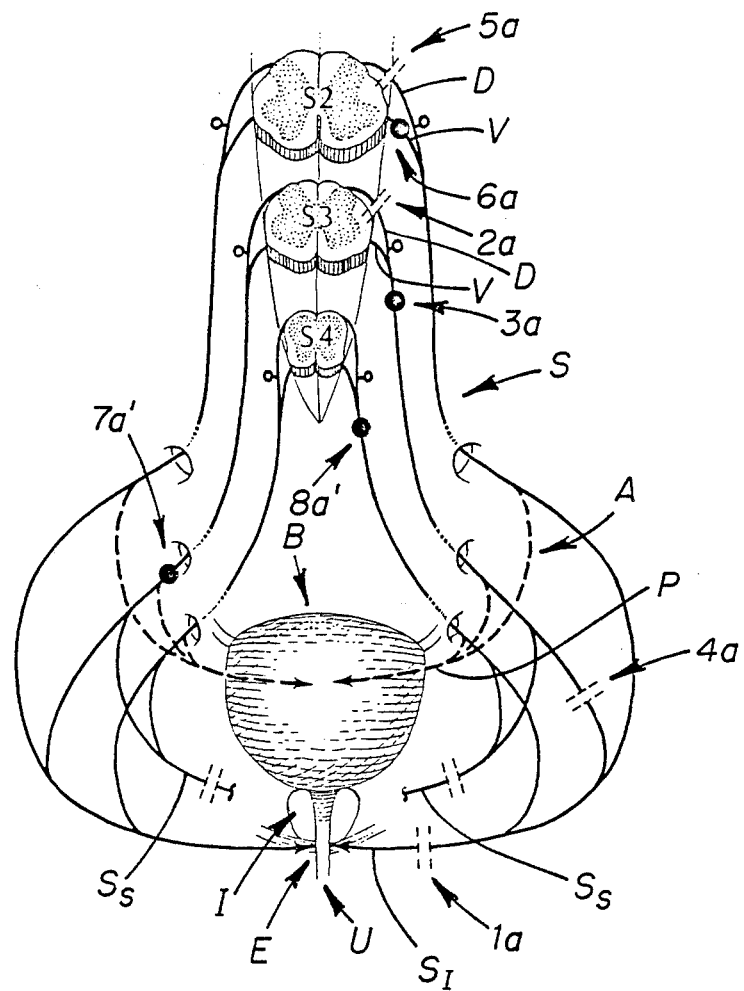
FIGS. 3 and 4 are views similar to FIG. 1, but illustrate additional operative procedures for controlling bladder evacuation and related functions.
Figure 4:
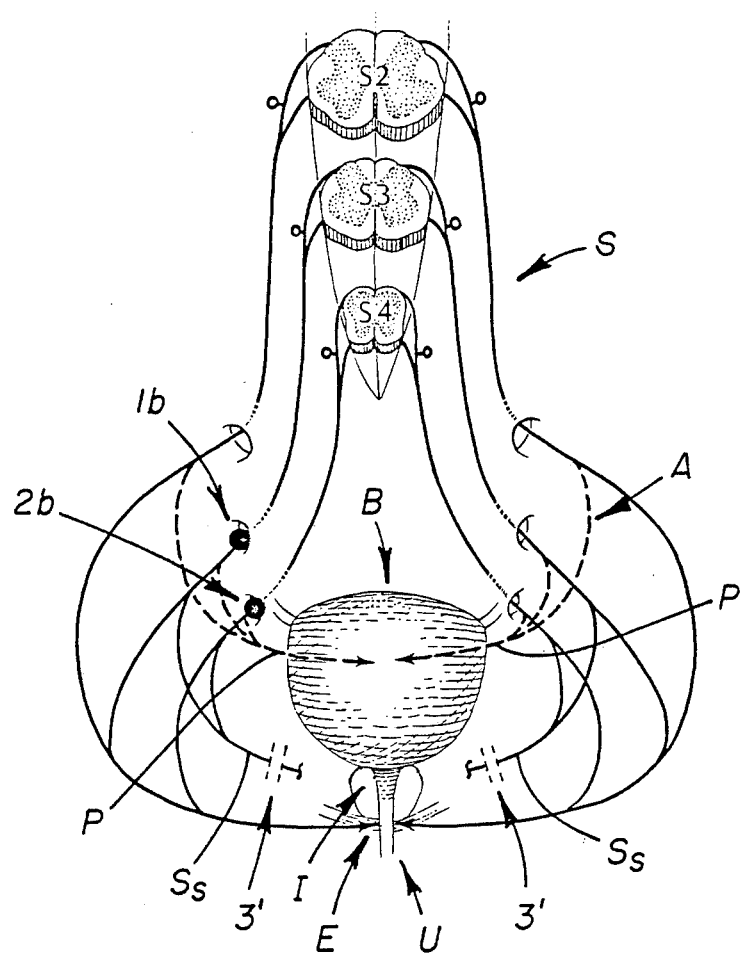
Figure 5:
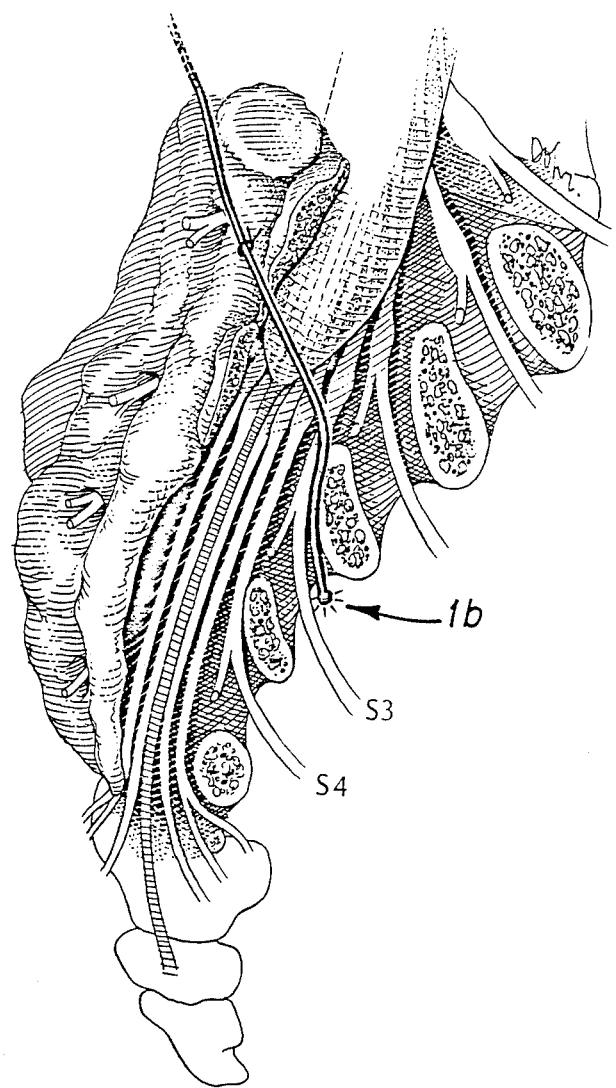
FIG. 5 schematically illustrates the percutaneous implantation of an electrode adjacent to the S3 sacral nerve through the dorsum for the purpose of selectively stimulating such nerve.
Figure 6:
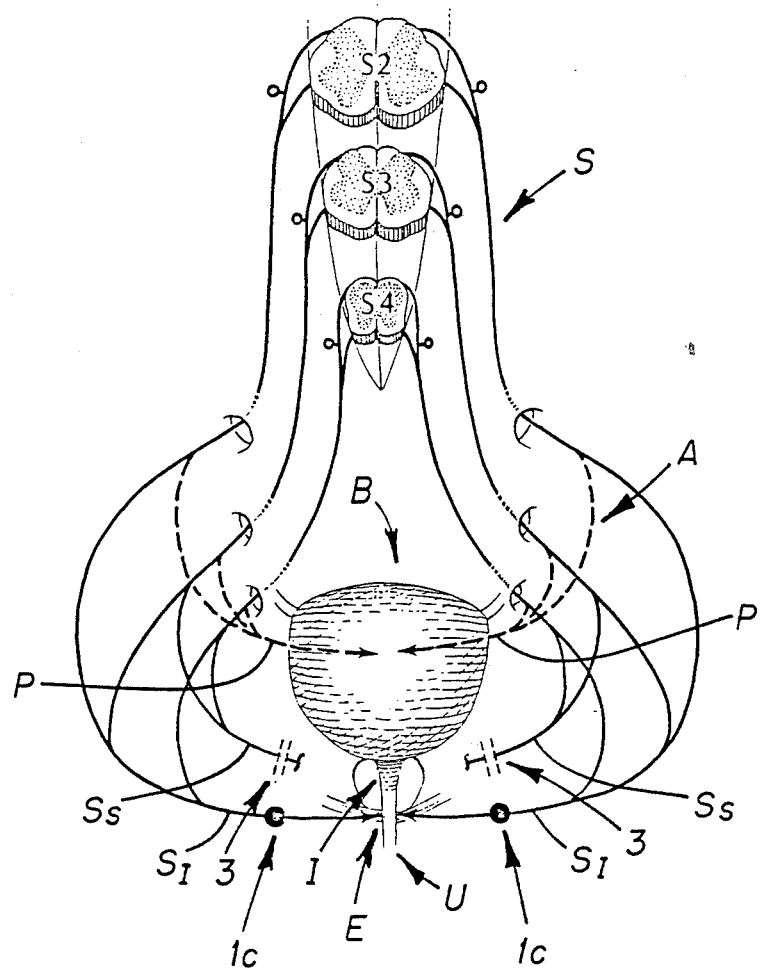
FIGS. 6–11 are views similar to FIG. 1, but illustrate additional operative procedures for controlling bladder evacuation and related functions.
Figure 7:
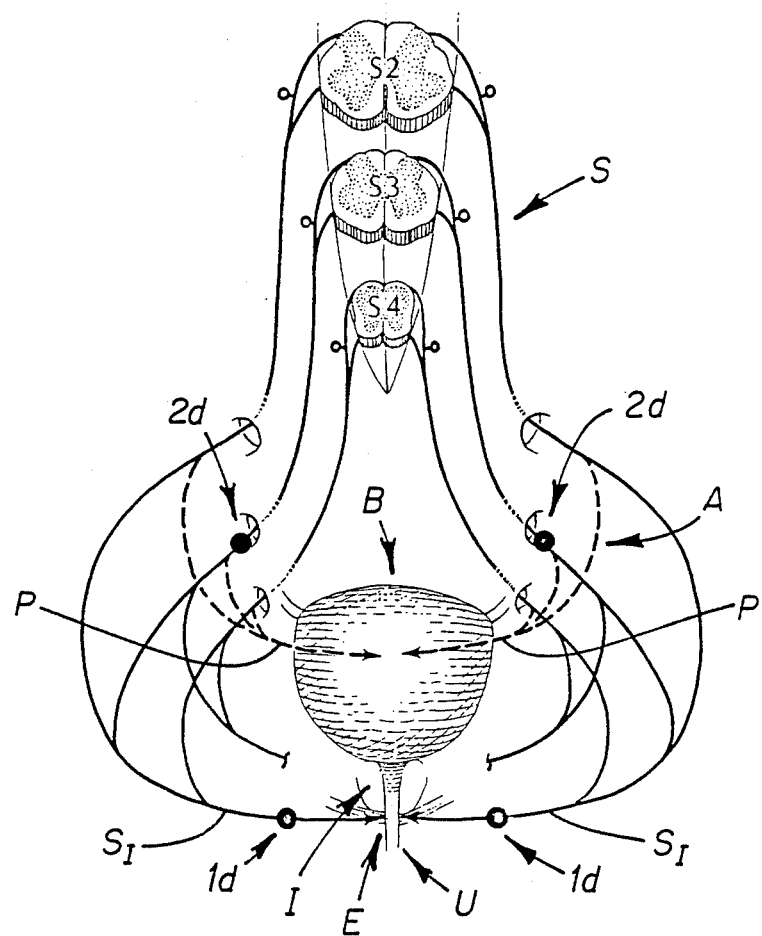
Figure 8:
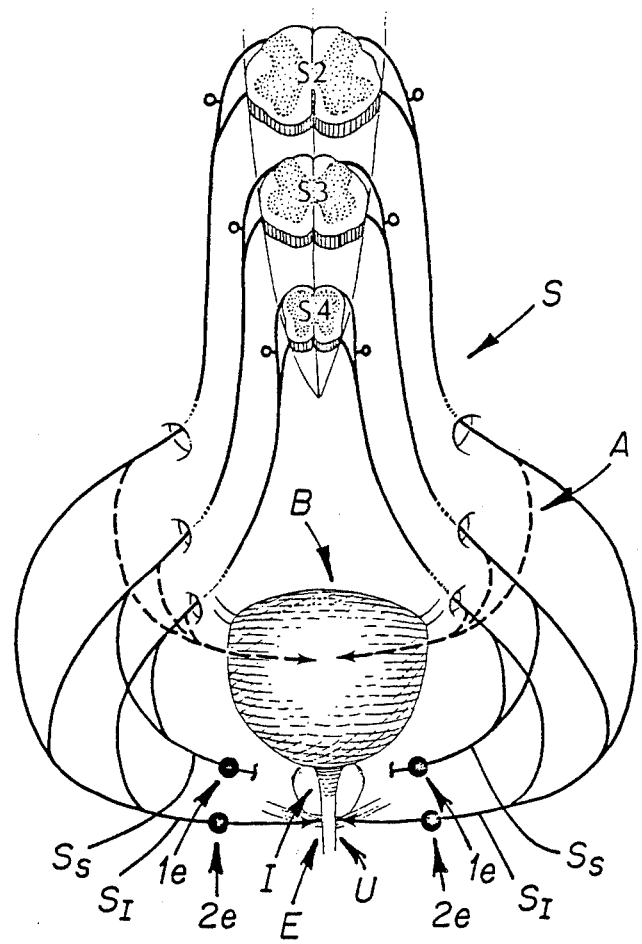
Figure 9:
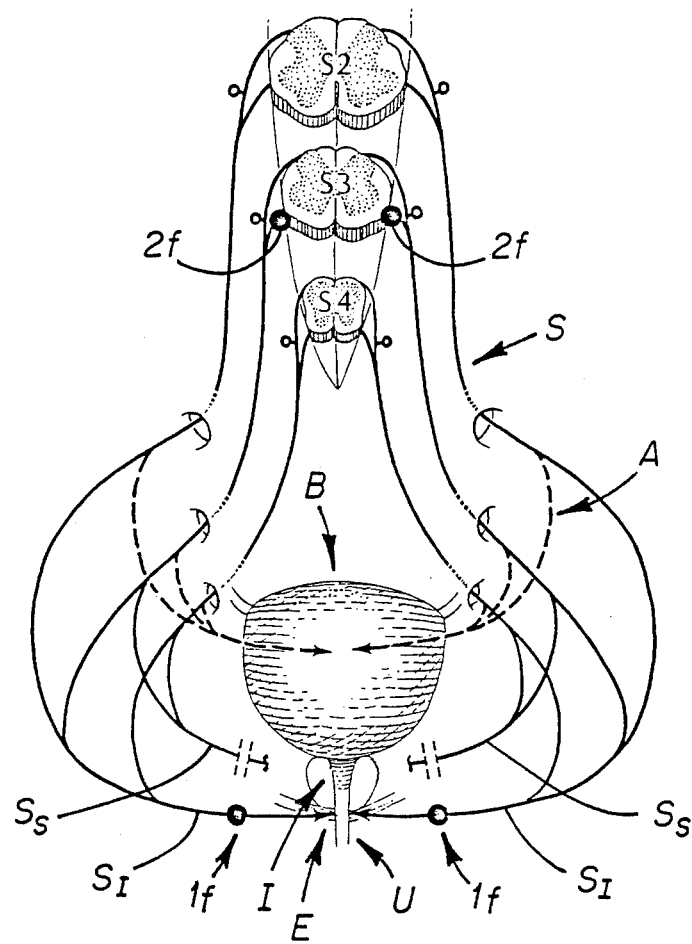
Figure 10:
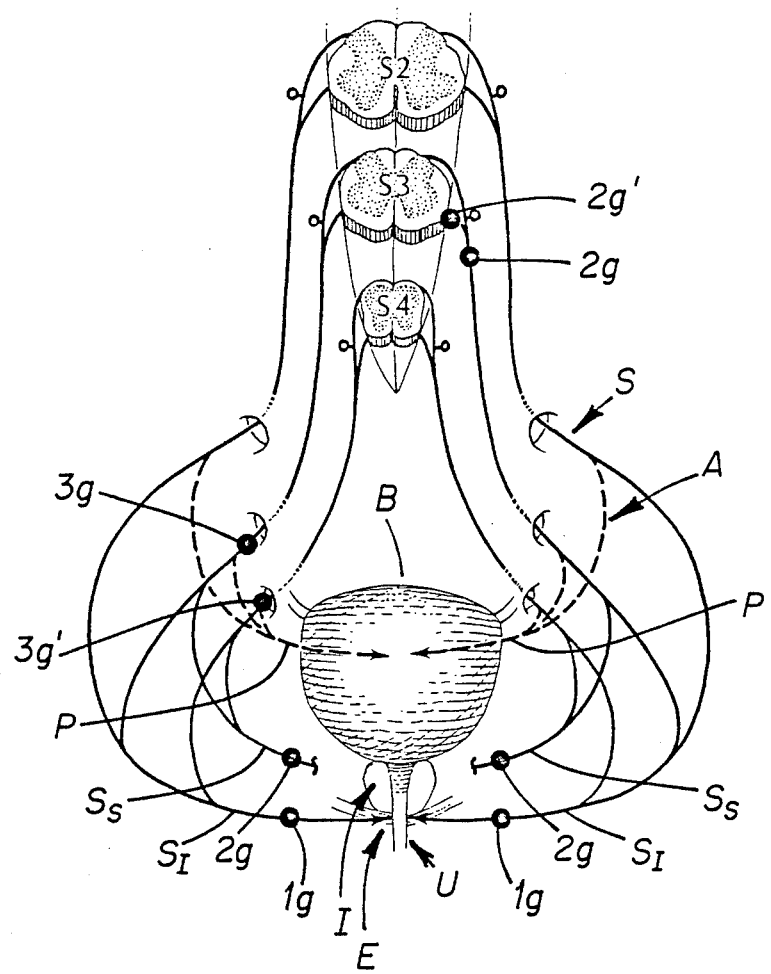
Figure 11:
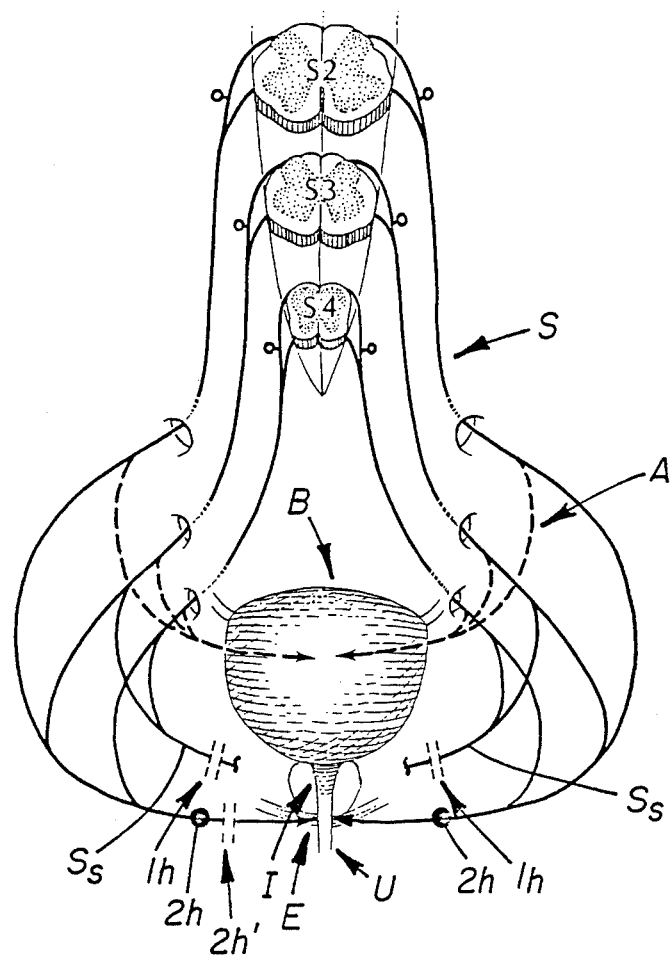
Figure 12:
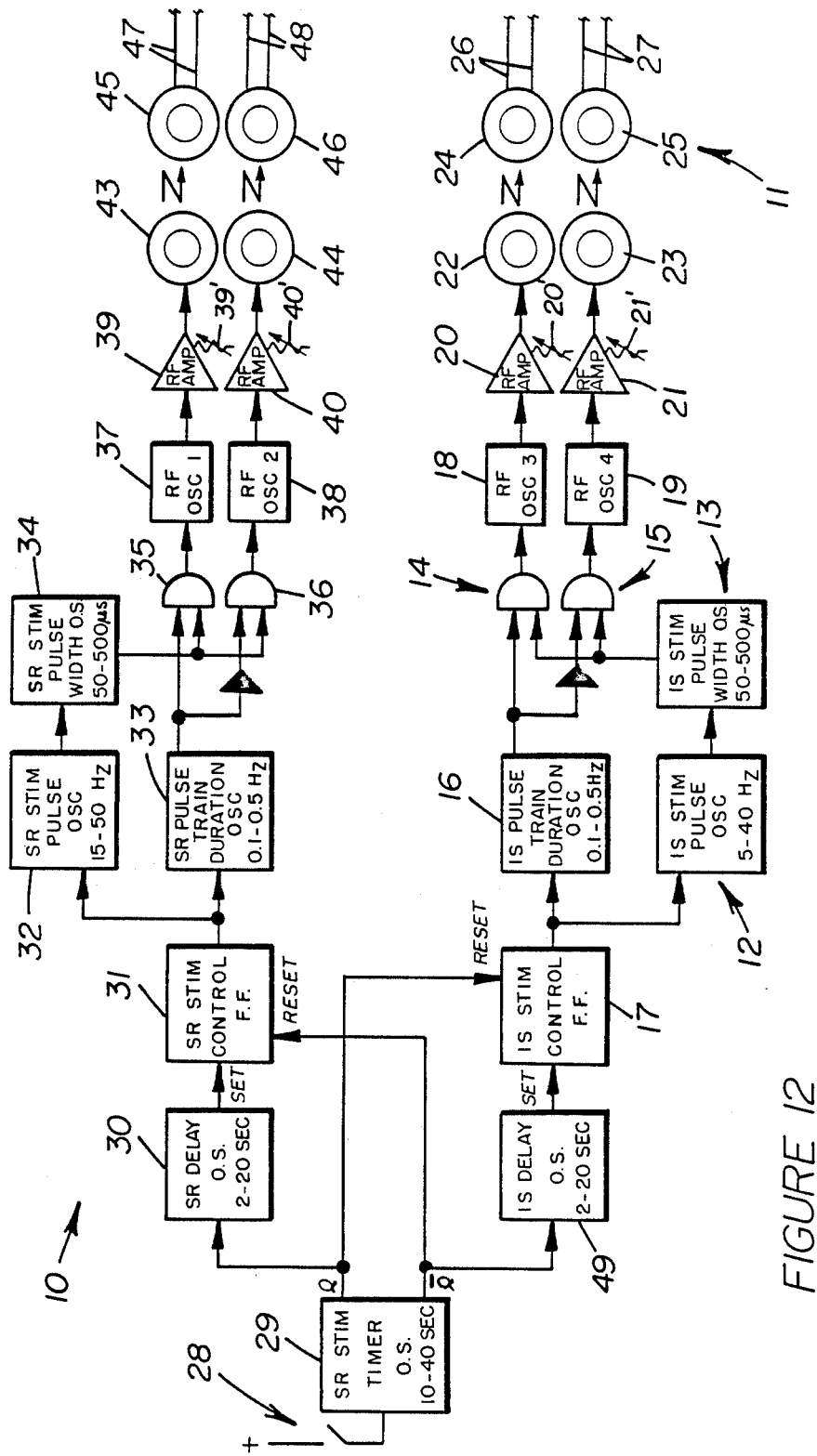
FIG. 12 illustrates a micturition control system adapted for use in conjunction with an operative procedure for controlling bladder and/or bowel evacuation and related functions.

As described in U.S. patent application Ser. No. 611,836, now U.S. Pat. No. 4,607,639, FIG. 1 schematically illustrates the pelvic plexus region of a human, including the nervous system for controlling bladder evacuation and related functions. The nervous system includes a somatic nerve system of fibers (or nerve bundles) S and an autonomic nerve system of nerve bundles A, finding their immediate origin at sacral segments S2, S3 and S4 of the spinal cord and sacrum, i.e., the triangular bone positioned below the lumbar vertebrae and comprising five fused sacral vertebrae that are wedge dorsally between the two hip bones. As illustrated in FIG. 2, the main nerve supply to the detrusor muscle of a bladder B emanates primarily from sacral segment S3, a lesser amount from sacral segment S2, and a still lesser amount from sacral segment S4, i.e., "response" refers to bladder response.

The application further teaches a method for controlling the evacuation of bladder B by first identifying the anatomical location of at least one nerve or component thereof that controls at least one function of the bladder, e.g., continence and/or contraction of the bladder. An electrode is then positioned, either surgically or percutaneously, at least in close proximity to the nerve and selectively energized to stimulate the nerve. Although the operative procedures, methods and systems described in the application were noted as being "particularly applicable to controlling bladder and related functions," it was further noted that "such procedures, methods and systems may also concurrently effect control of other organs, such as the bowel, colon and associated sphincters, (e.g., anus) and cuffs" and may be used to "normally provide means for eliminating or supressing spastic detrusor activity, spastic urethal and pelvic floor activity and spastic anal sphincter." Either permanent surgical implantation or temporary percutaneous implantation for nerve stimulation purposes was also taught.

As further illustrated in FIG. 1, the main nerve supply emanating from each sacral segment S2, S3 and S4 comprises two components or roots, namely, a dorsal root D and a ventral root V. The dorsal root is primarily sensory to transmit sensation to the spinal cord whereas the ventral root is primarily motor to transmit motor impulses from the spinal cord to bladder B and associated sphincter. Although illustrated as being separated, the dorsal and ventral roots for each nerve are, in fact, normally joined together and their fibers or bundles mixed to progress as a single trunk.

Bundles of the nerve trunk are divided into somatic nerve bundles S that connect to voluntary muscles and autonomic nerve bundles A that connect to visceral organs, such as bladder B. Dorsal root D can be separated from ventral root V since only stimulation of the motor nerve bundles of a particular ventral root are contemplated in many procedures. In this manner, the motor nerve bundles can be stimulated without inducing pain and without generating impulses along the sensory passageway.

Somatic nerves S and autonomic nerves A can also be separated from each other. For example, in a particular procedure wherein it is desireable to only drive muscles controlled by the somatic nerve, the somatic nerve can be solely stimulated. Should it prove desirable to control the muscles of only a visceral organ, such as the detrusor muscle of bladder B, the autonomic nerve bundles could be stimulated. Stimulation of the entire nerve trunk would function to stimulate each of the dorsal, ventral, somatic and autonomic nerve bundles.

FIGS. 1 and 3–11 illustrate various combinations of operative procedures for effecting the desired neurostimulation for specific case studies (male or female). For example, a quadriplegic who has suffered a neck injury and damage to his spinal cord will normally require an operative procedure wherein control of bladder B and external sphincter E are of utmost importance. In addition, the quadriplegic will suffer uncontrolled bowel evacuation, for example, which can be concurrently controlled when bladder control is effected by such operative procedure. In addition, it may prove desirable to modulate other voiding dysfunctions that may occur as a result of one or more of a multitude of other neurological reasons.

Thus, it is emphasized in applicants' parent application that the specific operative procedures therein described can be combined with one or more of the other procedures described therein, as dictated by pre-operative evaluation of responses to stimulation recorded urodynamically. For example, when a particular procedure (e.g., electrode implant, nerve separation, sectioning, etc.) is described as being performed bilaterally, clinical testing may indicate that in certain other patients, a unilateral procedure is necessary (and vice versa). Likewise, the specific steps or procedures utilized in one operative procedure (FIGS. 1 and 3–11) may be utilized in combination with one or more steps utilized in other operative procedures, as will be appreciated by those skilled in the arts relating hereto.

As further taught in applicants' parent application, although the operative procedures therein described are primarily useful and applicable to control of bladder functions, such procedures are concurrently applicable to the control of other organs, including the bowel and colon, associated sphincters (e.g., anus) and cuffs and to the elimination or supression of spastic detrusor activity, spastic urethal and pelvic floor activity and spastic anal sphincter. In all of the described operative procedures, it is assumed that pre-operative evaluation of response to stimulation has been recorded urodynamically to precisely locate the nerves requiring separation, neurostimulation and/or isolation, such as by sectioning.

Further details and description of the FIGS. 1 and 3–11 operative procedures, as well as those pertaining to the control system shown in FIGS. 12–17, are incorporated herein by specific reference to applicants' U.S. patent application Ser. No. 611,836, now U.S. Pat. No. 4,607,639.

ELECTRICAL CONTROL OF VISCERAL, VISCERO-SOMATIC, AND SOMATIC NEUROMUSCULAR DYSFUNCTIONS

The following description supplements that found in applicants' parent application. The physiology of the bladder and bowel is closely linked to the urethral muscle physiology of the pelvic floor and its related urethral and anal sphincters. The sequences for storage (continence) and evacuation suggest that the somatic muscles of the pelvic floor are principally responsible for both continence and evacuation. During the storage phase, the visceral organs, i.e., bowel/bladder, are either released from the reflex inhibition or are directly facilitated into contracting, or both. It has been determined that neural control of the pelvic muscles largely determines the state of activity of the pelvic viscera (bowel, bladder, and possibly erection). A simple example is the "hold" reflex used to suppress a strong urge to void or defecate at inconvenient times.

If the neural regulation of bladder and bowel activity is directly tied to that of the pelvic muscles in the normal, then it is most certainly tied to it in the abnormal. Just as the hold reflex is used to suppress an inconvenient urge to empty either the bladder or bowel, an electrically induced contraction of the pelvic sphincters can be used to suppress an overly active bladder or bowel.

There is a broad spectrum of patients who experience a multitude of symptoms resulting from dysfunctional behavior of the bladder, bowel, urethra, anal and pelvic floor muscle systems. Not uncommonly, the muscle dysfunction cannot be ascribed to any disease. The muscle dysfunction can, however, be very similar to that found for other neural disorders (e.g., meningomyelocele, hydrocephalus, spinal injury, multiple sclerosis, stroke, etc.). The visceral dysfunction can be demonstrated especially in the case of the bladder—to be associated with pelvic muscle dysfunction, with the behavior of the bladder being a direct result of excessive inhibition (e.g., inability to void completely because of an inability to relax the urinary sphincter completely), or excessive triggering of bladder contractions (i.e., a precipitate urge to void one's bladder) because of a breakdown in the efficiency of reflex coordination between the bladder and pelvic muscles. A similar analogy can be made for problems affecting the bowel (as well as erection). Correction of the pelvic muscle dysfunction can thus serve to correct the visceral muscle dysfunction. Other effects described by patients have included the reduction of severe neck spasm, back spasm and leg cramps.

Visceral muscle dysfunctions which can be considered a result of overfacilitated activity include the spastic colon, interstitial cystitis, detrusor instability, cardiovascular problems such as migraine headache or palpatations, and bladder retention syndromes. Somatic muscle dysfunctions directly resulting from poor neural regulation and overfacilitated behavior include: pelvic pain syndromes, frequency syndromes (pelvic floor and/or urethral instability), incontinency due to poor relaxation or instability of the sphincters (either bowel or bladder), and incontinence following prostatectomy.

Figure 18:
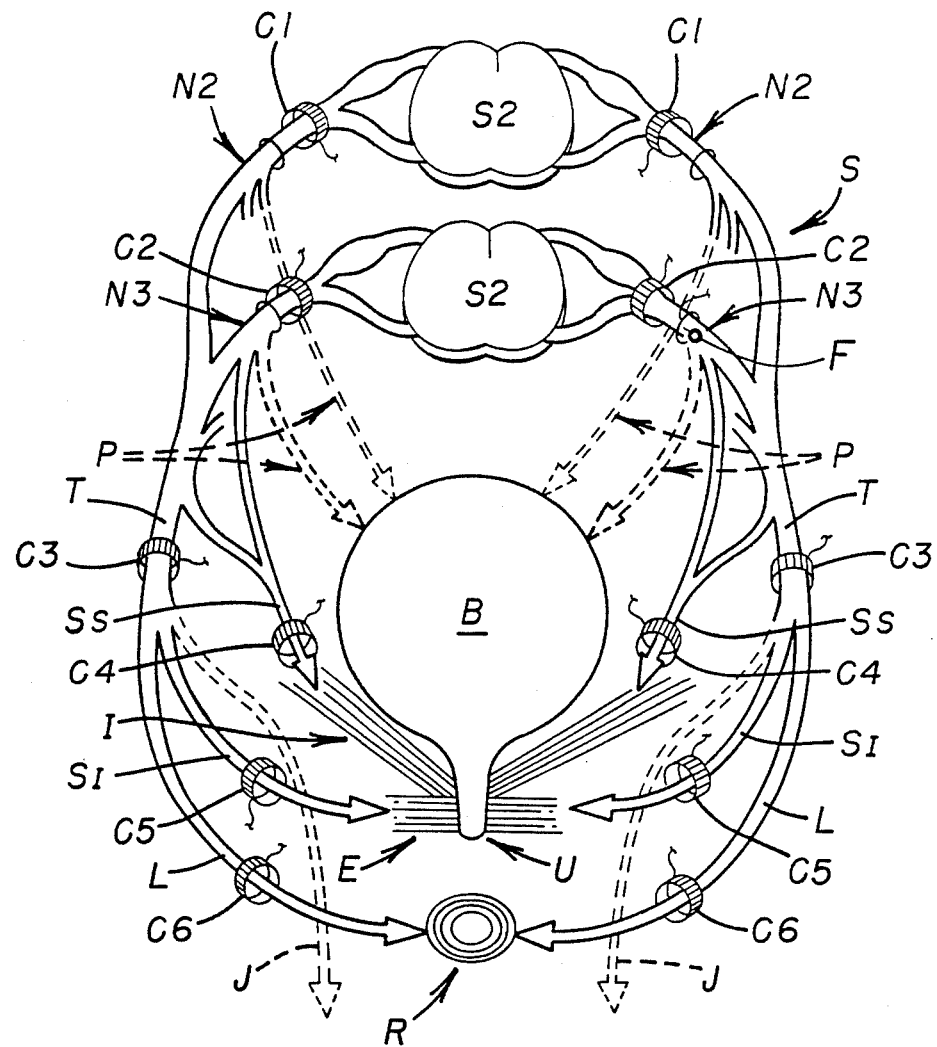
FIG. 18 is a view similar to FIG. 1, but illustrates the positioning of electrodes on various nerve bundles to effect desired results, as reflected in Charts I and II, set forth hereinafter.

Each of the above has been shown to respond to stimulation of the somatic muscles of the pelvic floor (primarily levator ani muscle I in FIG. 18). Neurostimulation of the pelvic muscles has a stabilizing effect on their neuro-regulatory mechanisms. Behavorial stabilization of pelvic muscles then affects the neuro control of the viscera.

Because of the similarity in nervous control between the bowel and bladder, the following bowel problems may also be treatable by a sacral or pudendal nerve electrode implant, namely, "spastic colon", and fecal incontinence either from spasticity or incompetence of the anal sphincter, and infrequent or too frequent bowel movements.

A spinoff benefit that has been noted is the treatment of foot drop. It appears that the planter flexion of the distal half of the foot and toes gives added stability to the gait. It has long been believed that foot drop was the result of a weakness in the muscles controlled by the perineal nerve. Stimulation of this nerve has been used to lift the foot using the foot dorsiflexors, but with limited success. Foot drop has been shown to improve by stimulation of sacral S3 nerve root N3 because of a better push the foot has as a result of planter flexion.

FIG. 18 illustrates letters depicting various components of the pelvic plexus region of a human that are common to those described in applicants' parent application. The following listing includes newly discussed components, shown in FIG. 18, as well as the common ones:

A: Autonomic nerve system.
B: Bladder.
C1–C6: Electrodes, shown as cuff electrodes for illustration purposes (other types could be used).
D: Dorsal root of nerve (sensory).
E: External sphincter of bladder B.
F: Foramen electrode.
I: Internal sphincter or levator ani muscle (pelvis floor, i.e., the composite muscular structure that constitutes the outlet of the boney pelvis and primarily consisting of the levator ani muscle).
J: Dorsal nerve of the penis.
L: Anal branch of pudendal nerve T.
N2, N3: Sacral nerves originating at sacral segments S2 and S3, respectively.
P: Pelvic nerves connected between the sacral nerves and the detrusor muscle of bladder B.
R: Anal sphincter (sphincter ani).
$S_I$: Inferior somatic nerve.
$S_S$: Superior somatic nerve.
T: Pudendal nerve.
U: Urethra.
V: Ventral root of nerve (motor).

Methods herein disclosed (Chart I) can be used to either modulate symptoms resulting from a loss of coordination between the normally synchronized functions of organs, including bladder B, rectum R and associated person's organs, including bladder B rectum R and associated sphincters:

| Organ(s) Affected | C1 Sacral Nerve N2 | C2 Sacral Nerve N3 | C3 Pudendal Nerve T | C4 Superior Somatic Nerves $S_S$ | C5 Inferior Somatic Nerve $S_I$ | C6 Anal Branch L |
|---|---|---|---|---|---|---|
| (1) B, E, R    | X |   | X |   |   |   |
| (2) B, E, R, I | X |   |   | X |   |   |
| (3) B, E, R    | X |   |   |   | X |   |
| (4) B, E, R    | X |   |   |   |   | X |
| (5) B, E, R, I | X |   | X | X |   |   |
| (6) B, E, R, I | X |   |   | X | X |   |
| (7) B, E, R, I | X |   |   | X |   | X |
| (8) B, E, R    |   | X | X |   |   |   |
| (9) B, E, R, I |   | X |   | X |   |   |
| (10) B, E, R   |   | X |   |   | X |   |
| (11) B, E, R   |   | X |   |   |   | X |
| (12) B, E, R, I |  | X | X | X |   |   |
| (13) B, E, R, I |  | X |   | X | X |   |
| (14) B, E, R   |   | X |   | X |   | X |
| (15) B, E, R   | X | X | X |   |   |   |
| (16) B, E, R, I | X | X |   | X |   |   |
| (17) B, E, R   | X | X |   |   | X |   |
| (18) B, E, R   | X | X |   |   |   | X |
| (19) B, E, R, I | X | X | X | X |   |   |
| (20) B, E, R, I | X | X |   | X |   |   |
| (21) B, E, R, I | X | X |   | X | X |   | bladder sphincters E and I and the anal sphincter for rectum R, or to treat incontinence by increasing sphincter tonus (Chart II). As described in the parent application, sacral nerves N2 and N3 originate at sacral segments S2 and S3, respectively, and form pelvic nerve P that controls contraction of a detrusor muscle surrounding bladder B. The sacral nerves also form somatic components that subdivide into: (1) superior somatic nerve $S_S$; and (2) pudendal nerve T that includes (a) inferior somatic nerve $S_I$ connected to muscles controlling external sphincter E of bladder B, (b) anal branch L connected to the anal sphincter for rectum R, and (c) dorsal nerve J connected to the penis. The nerve bundles connected to the various sphincters are controllable at a lower level of electrical stimulation than that required to control the muscles for the bladder and rectum proper.

FIG. 18 illustrates six cuff electrodes C1–C6 adapted to be positioned on selected nerve bundles (while simultaneously isolating adjacent nerve bundles) either individually or in combination with at least one other electrode for stimulation purposes. As described in the parent application, such positioning step occurs after identifying the anatomical location and functional characteristics of the selected nerve bundle or bundles. Pulse trains are then applied sequentially to the electrode or electrodes to control the function of the organ.

Individually, electrodes C1—C6 modulate or control the function(s) of the following organs:
C1: Bladder sphincter E, anal sphincter R and the detrusor muscle for bladder B.
C2: The detrusor muscle for bladder B and both bladder and anal sphincters E and R.
C3: Both bladder and anal sphincters E and R.
C4: Internal sphincter I (pelvic floor).
C5: Bladder sphincter E.
C6: Anal sphincter R.

CHART I

The following chart indicates twenty-one different combinations of electrode placement (unilaterally or bilaterally) for modulating the above-discussed symptoms resulting from a loss of coordination between a

CHART II

The following second chart indicates electrode placement (unilaterally or bilaterally) for treatment of incontinence by increasing sphincter tonus either by direct stimulation of a sphincter muscle or by modulating reflex control mechanisms so that more effective sphincter tonus results:

| Organ(s) Affected | C3 Pudendal Nerve T | C4 Superior Somatic Nerves $S_S$ | C5 Inferior Somatic Nerve $S_I$ | C6 Anal Branch L |
|---|---|---|---|---|
| (1) E, R | X |   |   |   |
| (2) I (Pelvic Floor) |   | X |   |   |
| (3) E |   |   | X |   |
| (4) R |   |   |   | X |
| (5) E, R, I | X | X |   |   |
| (6) I, E |   | X | X |   |
| (7) I, R |   | X |   | X |

The term "reflex control mechanisms" means those nerve bundles that control interrelated activity between bladder B and pelvic floor musculature (primarily levator ani muscle I) as they can reflexively influence each other by either inhibition or facilitation.

It should be noted in the charts that various electrode combinations may affect the identical organs, but to different degrees of intensity. For example, although electrode combinations (1) and (8) in Chart I each affect bladder B, bladder sphincter E and anal sphincter R, in combination (8) the bladder will be relatively more responsive since the main pelvic nerve supply P emanates primarily from sacral segment S3 and to a lesser amount from sacral segment S2.

The site or sites chosen for implantation of an electrode is determined by careful evaluation of a patient's problems. Such evaluations consist of symptom analysis, physical deficits or variations in muscle behavior of the lower extremities and pelvic muscles, or loss of sensation, the results of urodynamic testing and the results of test stimulation of the various sacral nerves. A temporary electrode is normally inserted percutaneously into one or more of the sacral foramena and specific nerve roots test stimulated for a response. When a desired response is obtained, a temporary electrode can be "floated" (e.g., Foramen electrode F in FIG. 18) in the vicinity of the nerve or nerves. This procedure allows the patient to have a three to five day trial of stimulation to evaluate the therapeutic benefits of stimulation.

Based on the response obtained with the test stimulation, the patient can be further evaluated for the response to be obtained by percutaneously implanting an electrode on one or more of the selected nerve bundles or an electrode can be permanently implanted, either via sacral laminectomy and placement of an electrode directly on a specific sacral nerve or by placing an electrode on the sacral foramen without performing a laminectomy. Therapeutic benefits are thus obtained by stimulation of specific pelvic muscles.

Applicants have further determined that the nerves controlling functions of the bladder also have a similar influence over the bowel. The same pathways and principles of stimulation described for control of the bladder also apply in respect to control of the bowel. Thus, the operative procedures described in applicants' parent application are equally applicable to bowel control.

We claim:

1. A method for modulating symptoms resulting from a loss of coordination between the normally synchronized functions of organs and for treatment of incontinence by increasing sphincter tonus either by direct stimulation of a sphincter muscle or by modulating reflex control mechanisms so that more effective sphincter tonus results, said organs including a bladder, a rectum and associated sphincters, in an anatomical system of a selected human, said system including S2 and S3 and S4 sacral segments of a spinal cord and a sacral nerve originating at each of said sacral segments, said sacral nerves forming a pelvic nerve when they leave the sacral canal, connected to said bladder to control contractions of a detrusor muscle thereof, and somatic components that subdivide into (1) a superior somatic nerve and (2) a pudendal nerve, including (a) an inferior somatic nerve connected to muscles controlling the external sphincter of said bladder, (b) an anal branch connected to an anal sphincter for said rectum, and (c) a dorsal nerve connected to a penis, the nerve bundle connected to said sphincters being controllable at a lower level of electrical stimulation than that required to control the functions of said bladder and rectum, said method comprising the steps of
identifying the anatomical location and functional characteristics of selected nerve bundles controlling the separate function of at least one organ of said organs,
positioning electrode means on said nerve bundles for electrically stimulating said nerve bundles while simultaneously isolating adjacent nerve bundles therefrom, and
applying pulse trains sequentially to said electrode means to separately control the function of at least said one organ.

2. The method of claim 1 positioning step comprises positioning at least two separate electrodes each on a separate nerve bundle and said applying step comprises applying coordinated and synchronized pulse trains sequentially or simultaneously to said electrode means to simultaneously and/or separately control the function of at least one of said organs.

3. The method of claim 2 wherein said positioning step comprises positioning a separate electrode on each of at least two separate nerve bundles, selected from the sacral nerve nerves originating at said sacral segments, said pudendal nerve, said superior somatic nerve, said inferior somatic nerve and said anal branch, for modulating symptoms resulting from a loss of coordination between the normally synchronized functions of said organs.

4. The method of claim 3 wherein said positioning step comprises positioning an electrode on each of said S2 sacral nerve and said pudendal nerve.

5. The method of claim 3 wherein said positioning step comprises positioning an electrode on each of said S2 sacral nerve and said superior somatic nerve.

6. The method of claim 3 wherein said positioning step comprises positioning an electrode on each of said S2 sacral nerve and said inferior somatic nerve.

7. The method of claim 3 wherein said positioning step comprises positioning an electrode on each of said S2 sacral nerve and said anal branch.

8. The method of claim 3 wherein said positioning step comprises positioning an electrode on each of said S2 sacral nerve, said pudendal nerve and said superior somatic nerve.

9. The method of claim 3 wherein said positioning step comprises positioning an electrode on each of said S2 sacral nerve, said superior somatic nerve, and said inferior somatic nerve.

10. The method of claim 3 wherein said positioning step comprises positioning an electrode on each of said S2 sacral nerve, said superior somatic nerve, and said anal branch.

11. The method of claim 3 wherein said positioning step comprises positioning an electrode on each of said S3 sacral nerve and said pudendal nerve.

12. The method of claim 3 wherein said positioning step comprises positioning an electrode on each of said S3 sacral nerve and said superior somatic nerve.

13. The method of claim 3 wherein said positioning step comprises positioning an electrode on each of said S3 sacral nerve and said inferior somatic nerve.

14. The method of claim 3 wherein said positioning step comprises positioning an electrode on each of said S3 sacral nerve and said anal branch.

15. The method of claim 3 wherein said positioning step comprises positioning an electrode on each of said S3 sacral nerve, said pudendal nerve and said superior somatic nerve.

16. The method of claim 3 wherein said positioning step comprises positioning an electrode on each of said S3 sacral nerve, said superior somatic nerve and said inferior somatic nerve.

17. The method of claim 3 wherein said positioning step comprises positioning an electrode on each of said S3 sacral nerve, said superior somatic nerve and said anal branch.

18. The method of claim 3 wherein said positioning step comprises positioning an electrode on each of said S2 and S3 sacral nerves, and said pudendal nerve.

19. The method of claim 3 wherein said positioning step comprises positioning an electrode on each of said S2 and S3 sacral nerves and said superior somatic nerve.

20. The method of claim 3 wherein said positioning step comprises positioning an electrode on each of said S2 and S3 sacral nerves and said inferior somatic nerve.

21. The method of claim 3 wherein said positioning step comprises positioning an electrode on each of said S2 and S3 sacral nerves and said anal branch.

22. The method of claim 3 wherein said positioning step comprises positioning an electrode on each of said S2 and S3 sacral nerves, said pudendal nerve, and said superior somatic nerve.

23. The method of claim 3 wherein said positioning step comprises positioning an electrode on each of said S2 and S3 sacral nerves and said superior somatic nerve.

24. The method of claim 3 wherein said positioning step comprises positioning an electrode on each of said S2 and S3 sacral nerves, said superior somatic nerve and said inferior somatic nerve.

25. The method of claim 3 wherein said positioning step comprises positioning said electrodes unilaterally on said separate nerve bundles.

26. The method of claim 3 wherein said positioning step comprises positioning said electrodes bilaterally on said separate nerve bundles.

27. The method of claim 1 wherein said positioning step comprises positioning at least one separate electrode on at least one nerve bundle selected from said pudendal nerve, said superior somatic nerve, said inferior somatic nerve and said anal branch and said applying step comprises treating incontinence by increasing sphincter tonus either by direct stimulation of the sphincter muscle or by modulating reflex control mechanisms so that more effective sphincter tone results.

28. The method of claim 27 wherein said positioning step comprises positioning an electrode on said pudendal nerve.

29. The method of claim 27 wherein said positioning step comprises positioning an electrode on said superior somatic nerve.

30. The method of claim 27 wherein said positioning step comprises positioning an electrode on said inferior somatic nerve.

31. The method of claim 27 wherein said positioning step comprises positioning an electrode on said anal branch.

32. The method of claim 27 wherein said positioning step comprises positioning an electrode on each of said pudendal nerve and said superior somatic nerve.

33. The method of claim 27 wherein said positioning step comprises positioning an electrode on each of said superior somatic nerve and said inferior somatic nerve.

34. The method of claim 27 wherein said positioning step comprises positioning an electrode on each of said superior somatic nerve and said anal branch.

35. A method for simultaneously controlling the coordinated and synchronized functions of a bowel and associated sphincter in an anatomical system of a selected human, said system including S2, S3 and S4 sacral segments of a spinal cord and a sacral nerve originating at each of said sacral segments and each of said sacral nerves including a dorsal root and a ventral root in a sacral canal, said sacral nerves forming a pelvic nerve when they leave the sacral canal connected to said bladder to control contractions of a detrusor muscle thereof, a superior somatic nerve and a pudendal nerve including an inferior somatic nerve connected to muscles controlling the external sphincter of said bladder, and an anal branch connected to an urethral said method comprising the steps of identifying the anatomical location and functional characteristics of those nerve bundles controlling the separate functions of said bowel and sphincter, separating motor, sensory and autonomic and somatic nerve fibers controlling the separate functions of the bowel and associated sphincter from other nerve fibers, positioning electrode means on selected ones of said nerve bundles for electrically stimulating such fibers while simultaneously isolating adjacent nerve fibers therefrom, and applying coordinated and synchronized pulse trains sequentially or simultaneously to said electrode means to simultaneously and/or separately control the functions of said bowel and sphincter.

* * * * *

UNITED STATES PATENT AND TRADEMARK OFFICE
CERTIFICATE OF CORRECTION

PATENT NO. : 4,739,764
DATED : APRIL 26, 1988
INVENTOR(S) : TOM LUE, ET AL.

It is certified that error appears in the above-identified patent and that said Letters Patent is hereby corrected as shown below:

COLUMN 9, LINE 64, AFTER "CLAIM 1" INSERT

--WHEREIN SAID--.

Signed and Sealed this

Eleventh Day of October, 1988

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,739,764

DATED : April 26, 1988

INVENTOR(S) : Tom Lue, et al.

It is certified that error appears in the above-identified patent and that said Letters Patent is hereby corrected as shown below:

The term of this patent subsequent to August 26, 2003, has been disclaimed.

Signed and Sealed this

First Day of November, 1988

*Attest:*

DONALD J. QUIGG

*Attesting Officer*  *Commissioner of Patents and Trademarks*